(12) United States Patent
Rzigalinski et al.

(10) Patent No.: US 7,534,453 B1
(45) Date of Patent: May 19, 2009

(54) CERIUM OXIDE NANOPARTICLES AND USE IN ENHANCING CELL SURVIVABILITY

(75) Inventors: Beverly A. Rzigalinski, Winter Springs, FL (US); Sudipta Seal, Oviedo, FL (US); David Bailey, Palm Bay, FL (US); Swanand Patil, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 830 days.

(21) Appl. No.: 10/655,143

(22) Filed: Sep. 4, 2003

Related U.S. Application Data

(60) Provisional application No. 60/408,275, filed on Sep. 5, 2002.

(51) Int. Cl.
*A01N 59/16* (2006.01)
*A61K 33/24* (2006.01)
(52) U.S. Cl. .................................................. 424/617
(58) Field of Classification Search ............. 514/769; 424/617; 435/1
See application file for complete search history.

(56) References Cited

U.S. PATENT DOCUMENTS

| | | | | |
|---|---|---|---|---|
| 5,910,311 A | 6/1999 | Boussouira | ............... | 424/401 |
| 5,961,993 A | 10/1999 | Boussouira | ............... | 424/401 |
| 6,103,247 A | 8/2000 | Boussouira | ............... | 424/401 |
| 6,316,012 B1 | 11/2001 | N'Guyen | ............... | 424/401 |
| 6,368,577 B1 * | 4/2002 | Kropf et al. | ............... | 424/59 |
| 6,406,685 B1 | 6/2002 | Philippe | ............... | 424/70.1 |
| 6,468,551 B1 | 10/2002 | Diec | ............... | 424/401 |
| 6,497,863 B1 | 12/2002 | Wachter | ............... | 424/65 |
| 6,497,865 B1 | 12/2002 | Griesbach | ............... | 424/70.1 |

OTHER PUBLICATIONS

Shui, Y.B. et al. "Morphological observation on cell death an dphagocytosis induced by ultraviolet irradiation in a cultured human lens epithelial cell line", Dec. 2000, vol. 71(6), abstract.*

* cited by examiner

*Primary Examiner*—Sreeni Padmanabhan
*Assistant Examiner*—Kendra D Carter
(74) *Attorney, Agent, or Firm*—Brian S. Steinberger; Joyce Morlin; Law Offices of Brian S. Steinberger, P.A.

(57) ABSTRACT

Novel, nonagglomerated, engineered, ultra fine Cerium Oxide particles the size of approximately 2 to approximately 10 nm and methods for preparation of the particles. The resultant particles enhance the longevity of cells in culture. Applications of the particles include benefits for wound healing, treating arthritis and joint diseases, anti-aging and the treating of inflammations.

4 Claims, 6 Drawing Sheets

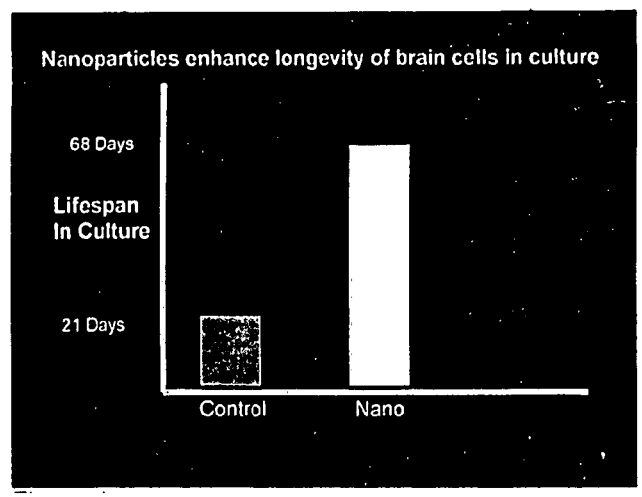
Fig. 1
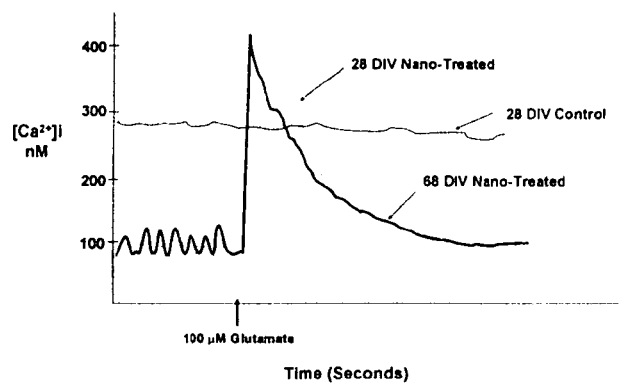
Fig. 2 Neurons in aged nano-treated cultures displayed normal spontaneous and glutamate-stimulated $[Ca^{2+}]_i$ elevations.

Nanoparticles decrease cell injury associated with exposure to UV light.

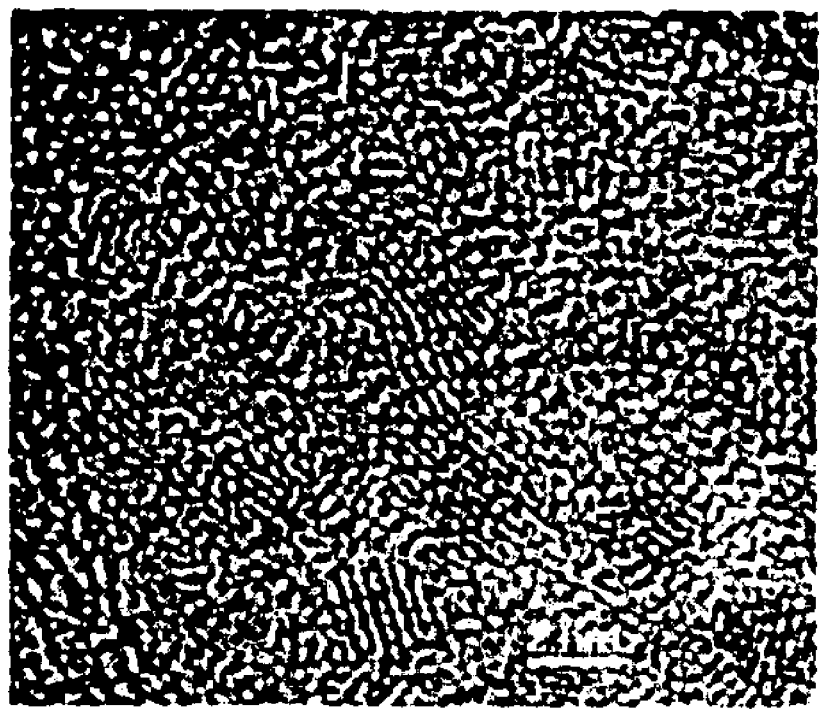
Fig. 5 Nanoparticles – 2-20 nm in solution

CERIUM OXIDE NANOPARTICLES AND USE IN ENHANCING CELL SURVIVABILITY

This invention claims the benefit of priority from U.S. provisional application 60/408,275 filed Sep. 5, 2002, and this invention was supported in part by the National Institute of Health (NIH), National Institute of Neurological Disorders and Stroke grant #NS40490 to B. Rzigalinski, and NIH National Institute of Aging grant #AG22617 to B. Rzigalinski. and National Science Foundation (NSF) grant number EEC: 0136710 to S. Seal.

FIELD OF THE INVENTION

This invention relates to novel cerium oxide nanoparticles and in particular to their use in the enhancement of survivability of biological cells, and methods of forming the nanoparticles.

BACKGROUND OF THE INVENTION

Earlier sol gel derived ceria nanoparticles between 0-100 mm are known, but it was very hard to achieve a stable suspension of non agglomerated particles. Particle agglomeration decreases the surface area of nanoparticles and may render them dysfunctional in some applications. For example, particles synthesized at 2-10 nm may agglomerate or clump, into particles with effective sizes much larger, thereby defeating the purpose of harnessing nanomaterial properties. Also, larger agglomerated particles appear to be unable to enter the cell, thereby losing their biological activity. Some oxide nanoparticles with sizes less than 10 nm may have a considerable amount of oxygen defects in their lattice structure which may be responsible for free radical scavenging. The present invention provides novel nonagglomerated engineered, ultra fine cerium oxide nanoparticles of the size of 2-10 nm.

It is a novel finding that exposure of the engineered, non-agglomerated ultra fine cerium oxide nanoparticles of 2-10 nm size of this invention to cells, enhances their lifespan in culture by acting as a regenerative free radical scavenger. Furthermore, these particles also have potent anti-inflammatory properties.

SUMMARY OF THE INVENTION

The first objective of this invention is to provide novel engineered cerium oxide nanoparticles.

The second objective of this invention is to provide a novel method for producing cerium oxide nanoparticles.

The third objective of the invention is to provide a method and composition for enhancing the longevity of living cells.

The fourth objective of the invention is to provide a method and composition for promoting wound healing.

The fifth objective of the invention is to provide a method and composition for treating arthritis and joint diseases.

The sixth objective of the invention is to provide an anti-aging treatment

The seventh objective of the invention is to provide a method and composition for treating inflammation.

The eighth objective of the invention is to provide surgical implants and dressings coated with Cerium oxide nanoparticles.

The invention encompasses nonagglomerated, ultra fine, engineered Cerium Oxide nanoparticles of the size approximately 2 to approximately 10 nm with high biological activity. Applications of the novel nanoparticles include surgical dressings, implants with the nanoparticles, and applications for wound healing, treating arthritis and joint diseases, anti-aging and the treating of inflammations.

A novel method for preparing Cerium Oxide nanoparticles of the size approximately 2 to approximately 10 nm can include the steps of dissolving approximately 0.5 to approximately 1.0 grams of $Ce(NO3)3.6H2O$ in deionized water to make approximately 10 mls of solution to form a first solution, followed by dissolving approximately 3 to approximately 4 grams of AOT(Na bis(ethylhexyl)sulphosuccinate) in approximately 200 ml of solvent to form a second solution, followed by combining the first and the second solutions, followed by stirring the combined solutions for approximately 30 minutes, and drop wise adding approximately 30% $H2O2$ until the stirred combined solution becomes yellow, and subsequently stirring for approximately 30 to approximately 60 minutes. Additionally, the method can include adding NaOH or NH4OH instead of $H2O2$.

Further objects and advantages of this invention will be apparent from the following detailed description of the presently preferred embodiments which are illustrated schematically in the accompanying drawings.

BRIEF DESCRIPTION OF THE FIGURES

FIG. 1 demonstrates the enhancement of longevity of brain cells in culture.

FIG. 2 shows neurons treated with Cerium Oxide nanoparticles display normal signaling functions.

FIG. 5 shows approximately 2 to approximately 10 nm Cerium Oxide nanoparticles in solution.

DESCRIPTION OF PREFERRED EMBODIMENTS

Before explaining the disclosed embodiments of the present invention in detail it is to be understood that the invention is not limited in its applications to the details of the particular arrangements shown since the invention is capable of other embodiments. Also, the terminology used herein is for the purpose of description and not of limitation.

The nanoparticles of the invention can be produced by a unique method. Nanoparticles of approximately 2 to approximately 10 nm are synthesized by a novel sol micro emulsion process to create nano reactors where the nanoparticles are synthesized. Importantly, the synthesis protocol renders the resulting particles with oxygen vacancies in their lattice structures where they have high biological activity as free radical scavengers. Their structure and mixed valence states also permits regeneration of the particles once a radical scavenging event has occurred, making them biologically available for multiple rounds of radical scavenging. This permits single doses of nanoparticles to remain active in the cell for long time periods. In contrast, most commonly available free radical scavengers such as vitamin E, nitrosone compounds, and vitamin C are inactivated after scavenging 1 free radical.

Nanoparticles produced by the unique chemical routes ranging from approximately 2 to approximately 10 nm were added to rat brain cell cultures in a single dose on day 2-10 in vitro, causing the cells to survive approximately 3-4 times longer than cells without nanoparticles, as demonstrated in FIG. 1. Additional experiments not shown in FIG. 1 have demonstrated that a single dose of cerium oxide nanoparticles produced in the method described above extended the life of cultured neurons from 28 days for untreated cells, to 182 days (6 months) for neurons treated with nanoparticles. Of critical importance was the fact that these aged neurons in all cases, were functional in signaling to one another and had active synaptic connections similar to young cultured neurons (FIG. 2).

Furthermore, they responded to the neurotransmitter glutamate, within the normal range of young, healthy, neurons.

Figure 3:
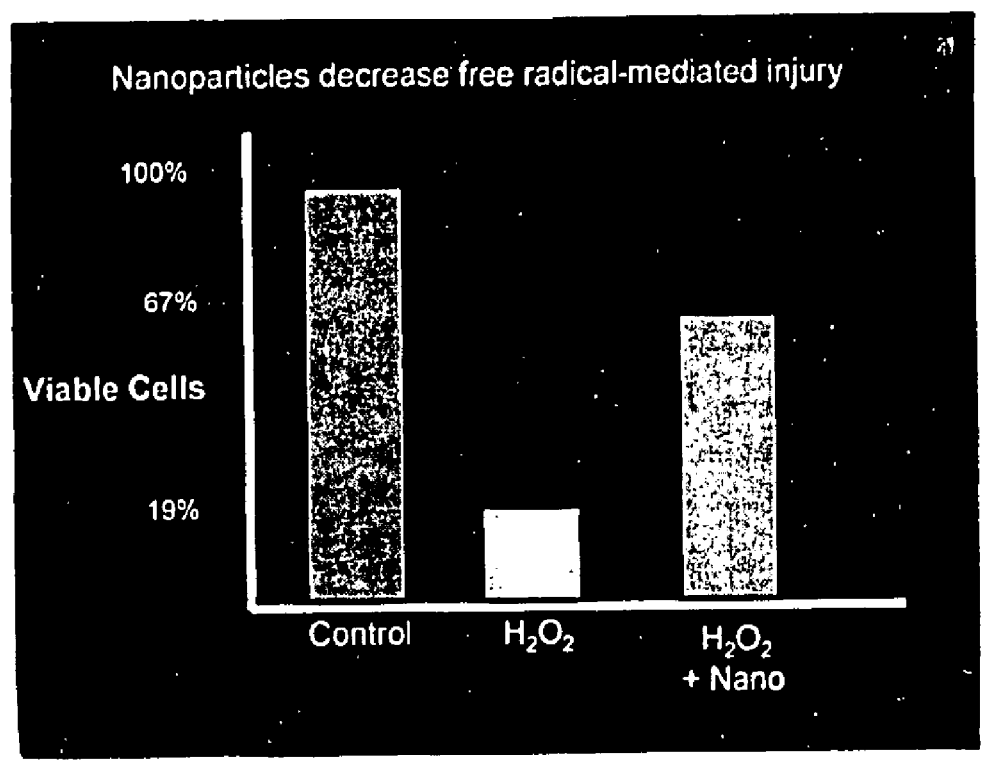
FIG. 3 demonstrates that nanoparticles decrease free radical-mediated injury.
Figure 4:
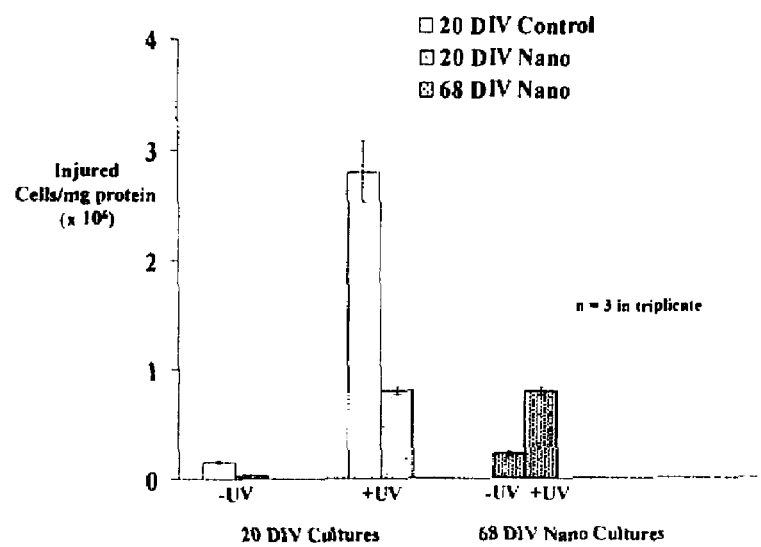
FIG. 4 shows nanoparticles decrease cell injury associated with exposure to UV light.

Given the structure of the cerium oxide nanoparticles and their surrounding lattice, it was hypothesized that the nanoparticles increased longevity by reducing the free radical damage to lipids, proteins, RNA and DNA, commonly associated with aging. To test this hypothesis, tissue cultured brain cells were exposed to a lethal dose of a free radical generating agent, hydrogen peroxide, and viability measured after a 1 hour exposure. Hydrogen peroxide exposure resulted in a dramatic decrease in viability. However exposure to cerium oxide nanoparticles afforded considerable protection to free radical induced cell death as demonstrated in FIG. 3. Additional experiments were conducted with a known free radical producing agent, ultraviolet light. Again, pretreatment of mixed brain cells cultures with cerium oxide nanoparticles decreased injury by over 60% (FIG. 4).

Figure 6A:
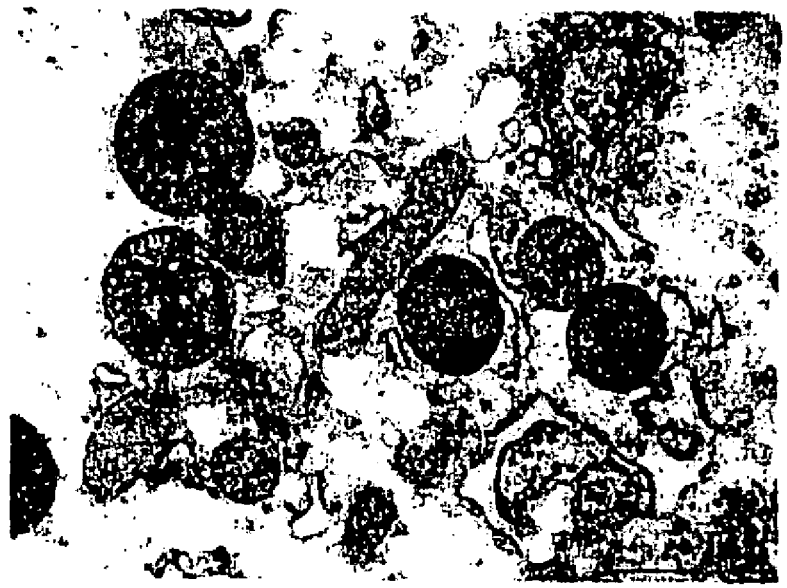
FIG. 6a shows cell cultures without nanoparticles.
Figure 6B:
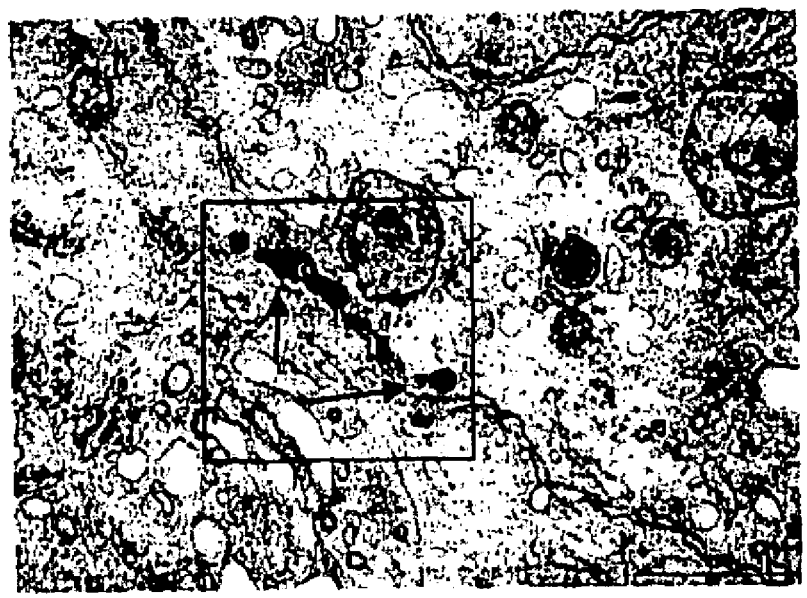
FIG. 6b shows cell cultures with nanoparticles.

Electron micrographs of approximately 2 to approximately 10 nm cerium oxide nanoparticles in solution are shown in FIG. 5 below. Additional electron microscopic studies were performed, to examine the location of nanoparticles in the cell cultures. As shown in FIGS. 6a and 6b, nanoparticles appear to be in the same focal plane as cellular organelles. In many cases, nanoparticles appeared to be in or near mitochondria, a site of high production of free radicals.

The data indicates that specifically engineered cerium oxide nanoparticles, produced by a process that enables biological activity, of a size of approximately 2 to approximately 10 nm can increase the longevity of cells in culture, possibly by acting as regenerative free radical scavengers. Vitamins E and C, and drugs such as polyethylene-glycol conjugated superoxide dismutase(Peg-SOD), have been tested as free radical scavengers to reduce injury and promote cell longevity. However neither of these compounds produces the dramatic effects observed with nanoparticles. Additionally, the nanoparticles of this invention are reported to be relatively inert in the body, with low toxicity. Tail vein injections of 0.3 mM nanoparticles (100 ul volume) produced no toxic effects. Therefore, this technology can provide significant improvement to medical conditions, as detailed below:

Wound Healing and Implants: Free radical damage is implicated in wound healing, and destruction of healthy tissue by free radicals generated during the inflammatory response is common. Nanoparticle coated implants or wound coatings can accelerate healing and prevent free radical damage to tissues.

Arthritis, Joint Disease: Free radicals produced by inflammatory processes by key components of tissue damage is arthritis and joint disease. The experiments indicate that cerium oxide nanoparticles dramatically reduced the inflammatory response in vitro. In inflammatory disease, healthy tissue damage often results from the by-products of inflammatory cells such as macrophages, partially through production of free radical species. In cultured inflammatory macrophage-like cells, cerium oxide nanoparticles reduced the inflammatory activation state and prevented bystander cell damage to healthy cells. Nanoparticle-coated metal/composite implants, or joint replacement material coated with nanoparticles, can substantially reduce tissue loss and damage in arthritis and other joint disease.

Vascular Disease: Vascular grafting with artificial vessels and stents is becoming increasingly common. However, a major reason for failure of vascular stents lies in the inflammatory reaction that these devices generate. Once again, a major component of initiation and propagation of the inflammatory response lies in production of free radicals and ensuing normal tissue damage. Coating of stents and other vascular replacements with cerium oxide nanoparticles can again decrease free radical damage commonly associated with vascular disease and reduce the inflammatory response.

Aging: A prevalent theory of aging is that accumulation of free radicals occurs, accompanied by a decline in the body in natural free radical reducing machinery. Engineered cerium oxide nanoparticles prepared by the present process results in high biological activity and can provide remediation for the increase in free radical damage associated with tissue aging and thereby reduce age-related functional disorders.

Figure 7:
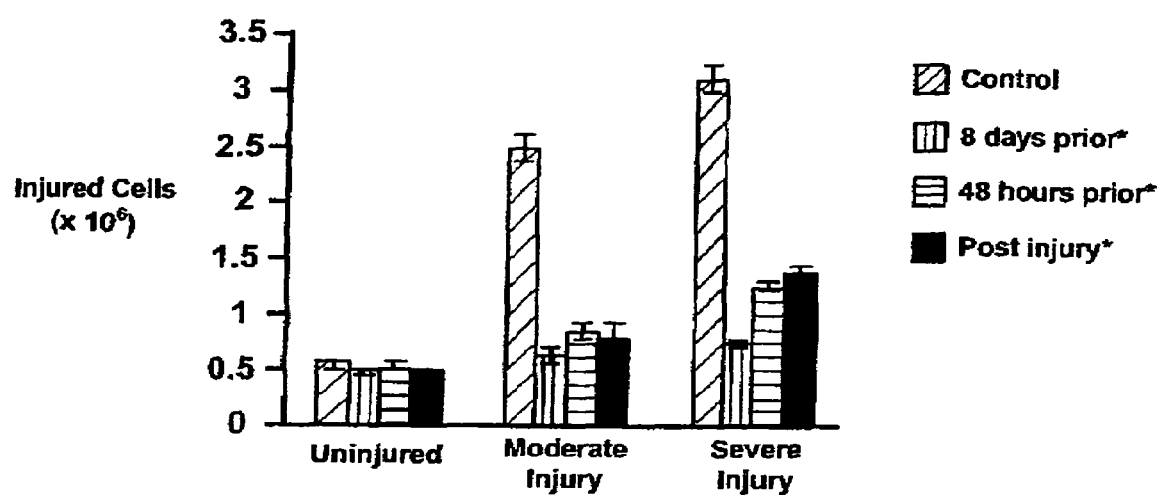
FIG. 7 shows that cerium oxide nanoparticles decrease brain cell injury after trauma.

Stroke and Traumatic Brain Injury: After traumatic brain injury and stroke, published reports indicate that a significant portion of tissue damage occurs due to production of free radicals. In vivo, brain cell death is often not evident until 24-48 hrs post injury (talk & die syndrome). The Rzigalinski lab routinely performs studies using a well-published in vitro model of traumatic brain injury, in which they have demonstrated a) Neuronal death 24 hr post injury and b) free radical production. Our engineered cerium oxide nanoparticles, when given to brain cells on day 2-10 in vitro, protected neurons from cell death associated with in vitro trauma. However, in real-world trauma or stroke, there is no opportunity to pre-treat individuals. Therefore, experiments were conducted to test whether nanoparticles could improve outcome if administered AFTER injury. As shown in FIG. 7, administration of engineered cerium oxide nanoparticles 1 hr post injury resulted in a significant reduction of cell death observed 24 hr after injury. The referenced asterick (*) in FIG. 7 refers to results when treatment includes the administration of engineered cerium oxide nanoparticles 8 days prior to an injury, 48 hours (2 days) prior to an injury and one (1) hour after an injury. The control example does not include the administration of engineered cerium oxide nanoparticles.

The Cerium Oxide nanoparticles of the invention can be administered to patients via oral pharmaceutical composition, or by intravenous injections or intrathecal delivery.

The following example is provided for the purpose of illustration and not limitation Example 1

The nanoparticles of the invention are prepared as follows:: A stable nano ceria sol is prepared using a micro emulsion technique. The principal of the micro emulsion technique involves the addition of a non-polar chemical (AOT) Na bis (ethylhexyl)sulphosuccinate) (also known as docusate sodium) which, when mixed with aqueous medium containing the cerium, forms a micro-reaction vessel. Thus, the AOT forms a micelle around the cerium particles, and the nanoparticle forms and grows with the surfactant shell. This process can be controlled to produce small (less than 10 nm) particles. By synthesis in the surfactant shell (technically termed reverse micelle) small sized particles are prevented from agglomerating in larger particles, with subsequent loss of activity. Specifically, 0.5-1.0 gm of $Ce(NO_3)_3 \cdot 6H_2O$ is dissolved in deionized water to make 10 ml of solution. In a separate beaker 3-4 gm of AOT(NNa bis(ethylhexyl)sulphosuccinate) is dissolved in 200 ml of toluene solvent. The cerium solution is added, and the emulsion is stirred for 30 minutes. Next, 30 ml of 30% H2O2 is added drop by drop. The solution turns yellow as soon as H2O2 is added and becomes deep as the reaction proceeds, taking approximately 30 to approximately 60 minutes to finish. The particles are approximately 2 to approximately 5 nm in this stable sol and the size can range from approximately 2 to approximately 10 nm. (Instead of H2O2, one can use NaOH or NH4OH for synthesis of cerium oxide nanoparticles.) For biological delivery, an approximately 0.1M solution was dried under nitrogen and resuspended in water to achieve the desired concentrations.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. A method for enhancing the survivability of living biological cells comprising:

selecting a plurality of living biological cells, wherein the cells are brain cells;

adding in-vitro, one single application of non agglomerated, ultra fine, engineered nanoparticles of cerium oxide of the size approximately 2 nm to approximately 10 nm wherein the nanoparticles contain a plurality of oxygen vacancies in a lattice structure and the oxygen vacancies support biological activity as free radical scavengers to cultures of the plurality of living brain cells; and enhancing a lifespan of the living brain cell cultures when the cerium oxide particles function as a regenerative free radical scavenger wherein after one free radical scavenging event has occurred, the cerium oxide particles remain biologically available for more than one free radical scavenging event.

2. The method of claim 1, wherein the living brain cells are from wounded brain tissues in the body.

3. A method for enhancing the survivability of living biological cells, in-vivo, comprising the steps of:

selecting a patient a brain injury vascular disease; and administering a medically effective amount of non agglomerated, ultra fine, engineered nanoparticles of cerium oxide of the size approximately 2 nm to approximately 10 nm, wherein the nanoparticles contain a plurality of oxygen vacancies in a lattice structure and the oxygen vacancies support biological activity as free radical scavengers to living brain cells, in-vivo, by coating and grafting at least one of a stent and other vascular replacements to decrease free radical damage associated with vascular disease and inflammatory response.

4. The method of claim 3, further comprising the step of administering the cerium oxide nanoparticles to the living brain cells, in-vivo, by at least one of oral pharmaceutical composition, intravenous injection and intrathecal delivery.

* * * * *